United States Patent
Johnson

(10) Patent No.: US 11,337,423 B1
(45) Date of Patent: May 24, 2022

(54) CANDIDA AURIS DISINFECTANT

(71) Applicant: Lanny Leo Johnson, Frankfort, MI (US)

(72) Inventor: Lanny Leo Johnson, Frankfort, MI (US)

( * ) Notice: Subject to any disclaimer, the term of this patent is extended or adjusted under 35 U.S.C. 154(b) by 0 days.

(21) Appl. No.: 17/363,682

(22) Filed: Jun. 30, 2021

(51) Int. Cl.
| | |
|---|---|
| *A61P 31/10* | (2006.01) |
| *A01P 3/00* | (2006.01) |
| *A61K 31/045* | (2006.01) |
| *A01N 37/10* | (2006.01) |
| *A61K 31/235* | (2006.01) |
| *A01N 31/02* | (2006.01) |
| *A01P 1/00* | (2006.01) |
| *A61K 31/192* | (2006.01) |

(52) U.S. Cl.
CPC ............ *A01N 37/10* (2013.01); *A01N 31/02* (2013.01); *A01P 1/00* (2021.08); *A01P 3/00* (2021.08); *A61K 31/045* (2013.01); *A61K 31/192* (2013.01); *A61K 31/235* (2013.01); *A61P 31/10* (2018.01)

(58) Field of Classification Search
CPC . A01N 37/10; A01N 31/02; A01P 1/00; A01P 3/00; A01P 31/10; A61K 31/045; A61K 31/192; A61K 31/235
See application file for complete search history.

(56) References Cited

U.S. PATENT DOCUMENTS

2014/0274973 A1 * 9/2014 Pedersen .................. A61P 31/12
514/160

OTHER PUBLICATIONS

Geng et al., Investigation on potential of Jinlianhua decoction against novel coronavirus (2019-nCoV) based on molecular docking. Open Access (OA) Online-First Publishing of Research Papers on COVI D-19, 2020, 1-16, 2020. Cited in copending U.S. Appl. No. 16/947,256.
Ku et al., Candida auris: Disinfectants and Implications for Infection Control. Frontiers in Microbiology, published: Apr. 12, 2018, doi: 10.3389/fmicb.2018.00726.
Maria Miklasinska, Antibacterial Activity of Protocatechuic Acid Ethyl Ester on *Staphylococcus aureus* Clinical Strains Alone and in Combination with Antistaphylococcal Drugs. Molecules 2015, 20, 13536-13549; doi:10.3390/molecules200813536.
Regina G. Dare, Abilities of protocatechuic acid and its alkyl esters, ethyl and heptyl protocatechuates, to counteract UVB-induced oxidative injuries and photoaging in fibroblasts L929 cell line. Journal of Photochemistry and Photobiology B: Biology, vol. 203,2020,111771, ISSN 1011-1344, doi.org/10.1016/j.jphotobiol.2019.111771.
Ryan Kean, The comparative efficacy of antiseptics against Candida auris biofilms. International Journal of Antimicrobial Agents doi: 10.1016/j.ijantimicag.2018.05.007.
Shi et al., Study on the overall regulation of Xuebijing injection in treating coronavirus disease 2019. Open Access (OA) Online-First Publishing of Research Papers on COVID-19, 2020, 1-7, 2020. Cited in copending U.S. Appl. No. 16/947,256.
Virginia Department of Health, Candida Auris Infection—Epidemiology. Nov. 2019.
Wikipedia, Alcohol. Last edited on Apr. 19, 2021, at 17:22 (UTC).
Wikipedia, Candida auris. Last edited on Jun. 15, 2021, at 01:56 (UTC).
Wikipedia, Disinfectant. Last edited on Jun. 1, 2021, at 10:00 (UTC).

* cited by examiner

*Primary Examiner* — Savitha M Rao
*Assistant Examiner* — Andrew P Lee
(74) *Attorney, Agent, or Firm* — Stonebridge IP, PLLC

(57) ABSTRACT

A method of disinfecting *Candida auris* is disclosed including treating a surface with a solution comprising 3,4-Dihydroxybenzoic acid ethyl ester. The solution may further include protocatechuic acid. The solution may include an alcohol. The alcohol may include methanol, ethanol, or isopropyl alcohol. The surface may include a solid surface, a porous or semi-porous surface, or a cloth-like surface. The surface may include a surface on skin, clothes, masks, a medical device, food processing equipment, hearing aid or a surgical implant. The surface may include a surface in a healthcare facility.

11 Claims, No Drawings

CANDIDA AURIS DISINFECTANT

BACKGROUND OF THE DISCLOSURE

Field of the Invention

This disclosure is directed to methods of disinfecting *Candida auris* with compositions including 4-dihydroxybenzoic acid ethyl ester.

Description of the Related Art

*Candida auris* is a rapidly emerging pathogen that causes severe infections with high mortality rates. It is frequently misidentified in clinical laboratories, thus requiring highly specialized identification techniques. Furthermore, it is believed to be potentially multidrug resistant and there is evidence of nosocomial transmission in outbreak fashion.

The effectiveness of disinfectant agents against *Candida auris*. is not well understood. Chlorine-based products may be effective for surface disinfection. Other disinfectants may have a role as adjunctive disinfectants. A cleaning protocol has also not been established and the use of disinfectants alone may not be sufficient for decontamination of patient care areas, for example, in healthcare facilities. Furthermore, the effectiveness of antiseptics against *Candida auris* is not known for patient decolonization and hand hygiene for healthcare personnel. There are reports of patients with persistent colonization despite twice daily body washes with disinfectant. Hand hygiene using soap and water, with or without chlorhexidine gluconate, may require the subsequent use of alcohol-based hand sanitizer for disinfection. *Candida auris* can spread by contact with contaminated surfaces in the environment. See e.g., *Candida auris*, Wikipedia, The Free Encyclopedia, date of last revision: 15 Jun. 2021, herein incorporated by reference; and *CANDIDA AURIS* INFECTION, Virginia Department of Health, Fact Sheet, downloaded from http://www.vdh.virginia.gov on Jun. 23, 2021, herein incorporated by reference.

Accordingly, new, and effective reagents against the pathogen *Candida auris* are urgently needed.

SUMMARY OF THE INVENTION

A method of disinfecting *Candida auris* is disclosed including treating a surface with a solution comprising 3,4-Dihydroxybenzoic acid ethyl ester. The solution may further include other anti-microbials; i.e., protocatechuic acid. The solution may include an alcohol. The alcohol may include ethanol, or isopropyl alcohol. The surface may include a solid surface, a porous or semi-porous surface, or a cloth-like surface. The surface may include a surface on skin, clothes, masks, a medical device, food processing equipment, or a surgical implant. The surface may include a surface in a healthcare facility.

Other features and aspects will be apparent from the following detailed description and the claims.

DETAILED DESCRIPTION

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

This disclosure is directed to the ethyl ester of 3,4-dihydroxybenzoic acid and its use as a disinfectant for *Candida auris*. Other names for this reagent include 3,4-Dihydroxybenzoic acid ethyl ester and EDHB Ethyl-3,4-dihydroxybenzoate (CAS 3943-89-3).

In embodiments, 3,4-Dihydroxybenzoic acid ethyl ester may be included in a solution with a solvent comprising an organic alcohol. Any known organic alcohol capable of dissolving 3,4-Dihydroxybenzoic add ethyl ester may generally be used with low boiling organic alcohols preferred, See Alcohol, Wikipedia, The Free Encyclopedia, date of last revision; 19 Apr. 2021, herein incorporated by reference. Preferably the alcohol may include ethanol, propanol, butanol, and/or isopropyl alcohol.

Two compounds involved in this disclosure are shown below.

Protocatechuic acid (PCA):

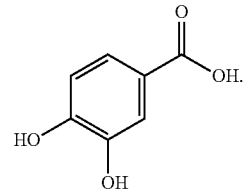 [SMILES: O=C(O)c1ccc(O)c(O)c1]

Ethyl ester of Protocatechuic acid:

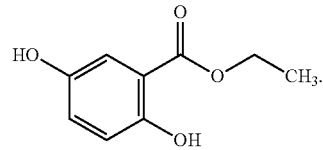

In one embodiment, the present disclosure provides an antimicrobial disinfectant composition including ethyl ester of protocatechuic acid; and optionally protocatechuic acid. Ethyl ester of protocatechuic acid has broad spectrum activity against disease-causing microbes including *Candida auris*. The present disclosure also provides for methods for disinfecting a surface or liquid, comprising contacting a surface or liquid with the disclosed disinfectant compositions. The disclosed methods may provide for the interruption of the transmission of *Candida auris* between mammals including human transmission.

In embodiments, the invention provides a method of disinfecting *Candida auris* comprising spraying a solution of up to 30% ethyl ester of protocatechuic acid in alcohol on a surface. In examples, the solution may comprise up to 99% alcohol, e.g., isopropyl alcohol or ethanol. The surface may be a solid surface, porous or semi-porous, or a cloth-like surface.

In one embodiment, means of delivery includes 3,4-dihydroxybenzoic acid ethyl ester in an alcohol solution. Upon contact with an article or surface, the alcohol disinfects the surface prior to evaporation, leaving behind a coating of 2,4 dihydroxybenzaldehye on the surface for an immediate and subsequent antimicrobial effect against recolonization of persistent organisms. The coating may be crystalline. In embodiments, the 3,4-Dihydroxybenzoic acid ethyl ester coating will continue to kill and protect the surface, or article of manufacture from *Candida auris* for a significant period of time up to at least 24 hours or more.

The present invention thus provides methods, compositions and uses for treating surfaces (solid, smooth, porous, or semi-porous, or cloth-like) and liquids to reduce *Candida auris* growth or to sanitize or sterilize the surface. More specifically, the methods and compositions described herein include contacting a surface with a composition including 3,4-dihydroxybenzoic acid ethyl ester thereby reducing or preventing *Candida auris* growth on the surface, and/or to sanitize or sterilize the surface. The surfaces can be in the health care setting, sports setting, including stadiums, or food preparation settings or any setting where sterile surfaces are required.

The compositions can be applied to solid surfaces such as implants, or solid surfaces like operating tables, benches, equipment, patient beds, etc., or surgical instruments to disinfect, sanitize, or sterilize the surface. Solid surfaces such as operating tables, other equipment and other surfaces can be treated as well by spraying of the surface with compositions comprising 3,4-dihydroxybenzoic acid ethyl ester. The surfaces may also include hearing aids, ear plugs, earphones and ear buds, and any other article that can be inserted into the ear. The surfaces may also include surfaces in (e.g., home, or commercial building) ventilation filters and in air conditioning ducts and components.

In embodiments, the compositions can be applied to smooth, porous, or semi-porous, or cloth-like surfaces such as wound dressings, bedding, vascular implants, bandages, etc. The material can be treated with the 3,4-dihydroxybenzoic acid ethyl ester solution and then used immediately, or the material can be allowed to dry and then used. For example, a bandage can be treated with 3,4-dihydroxybenzoic acid ethyl ester and then allowed to dry and store.

One embodiment of the present disclosure provides for the spraying of 3,4-dihydroxybenzoic acid ethyl ester in solution on a variety of articles. Upon drying the result being a coating of 3,4-dihydroxybenzoic acid ethyl ester on and or in the articles substance. The preferred embodiments are an article of manufacture including personal protective equipment (PPE). Personal protective equipment includes caps, hats, and other head coverings, gowns, masks and face-masks, gloves, shoes, and other footwear, etc. The application may be at the time of manufacture and or after-market application.

The products also include hard surfaces that are frequently touched or handled by the public. This would include, as nonlimiting examples, ATM machines and credit card payment devices, gas pump handles, doors and door-knobs, tables and counters in public spaces including restaurants, etc.

In embodiments, personal protective equipment may be coated or infused with 3,4-dihydroxybenzoic acid ethyl ester crystals. Coatings may be applied at the time of manufacture or after-market, i.e., while in use. In embodiments, an alcohol-based solution with 1 to 30% 3,4-dihydroxybenzoic acid ethyl ester may be used depending upon the intended application. The typical amount might be about 3% in a spray container, apparatus and/or mechanized delivery at manufacture of the article as with robotics and or assembly line.

In an embodiment, the alcohol vehicle causes an immediate 99% plus kill when wet. Upon drying, 3,4-dihydroxybenzoic acid ethyl ester remains as an anti-bacterial coating. 3,4-dihydroxybenzoic acid ethyl ester in this form on metal and or cloth destroys the bacteria on contact. The anti-bacterial function may be based upon the 3,4-dihydroxybenzoic acid ethyl ester crystals in solution, and or dry, and cause the bacteria to be disinfected upon contact.

Further, the compounds of this invention will be between 20-30% by weight of the compound for one intended use and more preferably, between 1% and 30% by weight of the compound depending upon the chemical nature of the vehicle.

Further, the methods and compositions described herein include adding the composition comprising 3,4-dihydroxybenzoic acid ethyl ester thereof to liquid or fluid, including other sanitizing solutions and/or sanitizing components. Further still, the methods and compositions described herein include adding the composition comprising 3,4-dihydroxybenzoic acid ethyl ester to any other vehicle, including but not limited to a powder, paste, cream foam, gel, wipes, other sanitizing components and the like thereby killing, reducing, or preventing *Candida auris* on said surface.

The present invention provides a composition that destroys *Candida auris*. The composition may further include protocatechuic acid (PCA). The 3,4-dihydroxybenzoic acid ethyl ester may be mixed with 70% isopropyl alcohol or ethanol and or a small amount of essential oil, i.e., lemon, peppermint, etc. The concentration of 3,4-dihydroxybenzoic acid ethyl ester can be anywhere from about 20% by weight to 100% by weight. Preferably the concentration of 3,4-dihydroxybenzoic acid ethyl ester varies with the intended purpose from 1%, 20%, 30%, 20-50% or 20-40% or 20-30% by weight.

The amount of 3,4-dihydroxybenzoic acid ethyl ester necessary for coating metal and or cloth may be 20 to 30% or 20-30 grams per 100 ml of 70% isopropyl alcohol or ethanol. These compositions allow for higher concentrations and evaporate rapidly to dry state on the surface or cloth.

In another aspect of the present invention, a method of disinfecting a surface comprising contacting said surface with 3,4-dihydroxybenzoic acid ethyl ester is contemplated.

This disclosure also provides for a method including contacting a surface with an effective amount of the composition. By the term "effective amount" of a composition as provided herein is meant an amount of a composition sufficient to provide the desired benefit. As disclosed herein, the exact amount required will vary from use to use depending on a variety of processing parameters, as understood by one of ordinary skill, such as the application, type of surface, the surface size, the mode of delivery (e.g., aerosol, spraying or dipping), and the like. Determination of what constitutes an "effective amount" is made by routine testing with known concentrations and adjusting those concentrations as needed to obtain the desired benefit and can be determined by one of ordinary skill in the art using routine experimentation so that the 3,4-dihydroxybenzoic acid ethyl ester disinfects *Candida auris*.

When the composition of this invention is applied to a surface to be treated, the composition generally can include a concentration of the 3,4-Dihydroxybenzoic acid ethyl ester not including the carrier between 90%-97% by weight of the compound, and more preferably, between 95%-98% by weight.

When the composition or compositions of this invention are applied to a surface to be treated, they may be diluted for use as a sanitizer.

In another aspect, the invention provides a method of inhibiting *Candida auris* on a solid, smooth, porous, or semi-porous, or cloth-like surface (such as but not limited to a cloth, wound dressing, bandage, heart or vessel grafts) by treating the surface with a composition of the present invention.

The present invention thus provides a composition that destroys or inhibits *Candida auris*. The 3,4-Dihydroxybenzoic acid ethyl ester may be mixed with 70% isopropyl alcohol. The concentration of 3,4-Dihydroxybenzoic acid ethyl ester can be anywhere from about 20% to 100% by weight. Preferably the concentration of 3,4-Dihydroxybenzoic acid ethyl ester is about 20-50% by weight or is about 20-40% by weight or is about 20-30% by weight or is 30% to 50% by weight.

The invention provides another composition comprising about 17 to 40%, or 17 to 30% or 17 to 20% by weight of 3,4-Dihydroxybenzoic acid ethyl ester, isopropyl alcohol and/or ethanol, propylene glycol and an essential oil, preferably of peppermint, or a citrus fruit (i.e., lemon, grapefruit, orange, lime, etc.). This composition is useful in the methods described in the invention, for example as a skin antiseptic as a surface disinfectant, as a spray to disinfect a surface, etc. The composition of the invention, may have at least 3,4-dihydroxybenzoic acid ethyl ester at 17+% by weight in at least 70-90% isopropyl alcohol or ethanol, propylene glycol (15 mls in a 105 ml total solution) and essential oil; i.e., peppermint or lemon etc.

The invention further provides a composition of 3,4-dihydroxybenzoic acid ethyl ester wherein the composition comprises or consists of 3,4-dihydroxybenzoic acid ethyl ester that can be applied directly or provided in various vehicles depending upon the application. A composition of 70% isopropyl alcohol and/or ethanol, propylene glycol and essential peppermint oil may be effective in use as a skin antiseptic. Higher concentration of 10% 3,4-dihydroxybenzoic acid ethyl ester (20 grams in 90 milliliters of 70% isopropyl alcohol) may be more effective. The following concentration may also be effective—the composition comprising or consisting of 3,4-Dihydroxybenzoic acid ethyl ester (20 grams) 70% isopropyl alcohol and/or ethanol (85 ML), propylene glycol (15 ml) and an essential oil (5 ml).

In addition to the components and administration of said compositions disclosed above, the compositions can be in the form of a solution and deliver 3,4-dihydroxybenzoic acid ethyl ester in suspension and or upon drying produce a residual 3,4-dihydroxybenzoic acid ethyl ester coating. The compositions disclosed herein can also be in the form of a liquid, gel, suspension, dispersion, solid, emulsion, aerosol, for example, powders, tablets, capsules, pills, liquids, suspensions, dispersions, or emulsions. Also, the compositions disclosed herein can be in the form suitable for dilutions. Similarly, the compositions can be in the form of a powder, cream, paste, gel or solid that can be reconstituted.

In embodiments a solution of the disclosure may include only 3,4-Dihydroxybenzoic acid ethyl ester and a carrier, preferably an alcohol carrier as described herein.

Other components can be present in the composition, if desired as well. For example, the composition can also include at least one additive selected independently from a carrier, a diluent, an adjuvant, a solubilizing agent, a suspending agent, a filler, a surfactant, an antimicrobial agent, a preservative, a viscosity modifier, a thixotropy modifier, a wetting agent, an emulsifier, or any combinations thereof. For example, the disclosed compositions can further comprise at least one surfactant selected from a cationic surfactant, an anionic surfactant, a non-ionic surfactant, and an amphoteric surfactant. Additionally, the disclosed compositions may further comprise medicament is selected from the group consisting of burn relief medications, anesthetic agents, wound cleansers, antiseptic agents, scar reducing agents, immunostimulating agents, anti-bacterial agents, biofilm destroying agents, antiviral agents, anti-keratolytic agents, anti-inflammatory agents, antifungal agents, acne treating agents, sunscreen agents, dermatological agents, antihistamine agents, antibacterial agents, bio adhesive agents, inhibitors of prostaglandin synthesis, antioxidants, and mixtures thereof.

In another embodiment, compositions of the present invention are formulated for use in liquids, solutions, gels, soaps, creams, powders, salves, and other preparations designed for topical use as antiseptic agents, sprays, foams, antibacterial treatments, wipes, and the like. In another embodiment, antiseptic compositions of the present invention are formulated as a hand antiseptic, sanitizer, or disinfectant.

In yet another embodiment, sanitizing compositions of the present invention are formulated for use in liquids, solutions, gels, soaps, and other preparations designed for use as sanitizing agents, liquids, including sprays, foams, gels, soaps, sanitizing treatments, and the like when used as a sanitizing solution, including but not limited to, use in food processing facilities, including food-processing equipment and utensils, and on other food-contact articles.

In yet another embodiment, sanitizing compositions of the present invention use in food processing facilities, including food-processing equipment and utensils, and on other food-contact articles are formulated to include any components generally recognized as safe for use in food processing facilities, including but not limited to, aqueous solutions containing potassium, sodium or calcium hypochlorite, a solution of hydrogen peroxide, an aqueous solution containing potassium iodide, sodium lauryl sulfate, sodium-toluenesulfonchloroamide, solutions containing dodecylbenzene sulfonic acid, other acceptable detergents and the like.

In yet another aspect, the compositions of the present invention are used in food processing, including cold sterilization of food containers, including bottles, without causing undesirable effects or interacting in a deleterious manner.

In examples, the compositions disclosed herein can further comprise a carrier or vehicle. The term "carrier or vehicle" means a compound, composition, substance, or structure that, when in combination with a compound or composition disclosed herein, facilitates preparation, administration, delivery, effectiveness, or any other feature of the compound or composition. Examples of carriers include isopropyl alcohol, ethanol, polyols (propylene glycol, polyethylene glycol, glycerol, and the like), vegetable oils, and suitable mixtures thereof.

In a further example, the compositions disclosed herein can also comprise adjuvants such as preserving, wetting, emulsifying, suspending agents, and dispensing agents.

Suitable suspending agents can include, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The disclosed compositions can also comprise solubilizing agents and emulsifiers, as for example, ethyl alcohol, isopropyl alcohol, ethyl carbonate, ethyl acetate, benzyl alcohol, benzyl alcohol, benzyl benzoate, propylene glycol, 1,3-butyleneglycol, dimethylformamide, oils, in particular, cottonseed oil, groundnut oil, corn germ oil, olive oil, castor oil and sesame oil, glycerol, tetrahydrofuran fury 1 alcohol, polyethylene glycols and fatty acid esters of sorbitan, or mixtures of these substances, and the like. The additives can be present in the disclosed compositions in any amount with the 3,4-dihydroxybenzoic acid ethyl ester.

By "disinfect" or other forms of the word, such as "disinfectant" or "disinfecting," is meant decrease or lower a characteristic (e.g., eliminate, reduce, inhibit, decrease, or prevent) viral growth, viability, or survival at any concentration. It is generally understood that disinfect involves providing an effective amount of the composition to any surface, but particularly solid surfaces, whether smooth or porous or semi-porous, or cloth-like surfaces. See e.g., Disinfectant, Wikipedia, The Free Encyclopedia, date of last revision: 1 Jun. 2021, herein incorporated by reference.

By "sanitize" or other forms of the word, such as "sanitizer" or "sanitizing," is meant decrease or lower a characteristic (e.g., eliminate, reduce, inhibit, decrease, or prevent) bacterial growth, viability, or survival at any concentration. It is generally understood that sanitizing involves providing an effective amount of the composition to any surface. Further, it is generally understood that sanitizing solutions and sanitizing components are those solutions that may be safely used on food-processing equipment and utensils and on other food-contacting conditions.

By "sterilize" it is meant to kill on the article being sterilized. Sterilize and sterilization include cold sterilization methods.

The term 'room' generally means an enclosed space in a building particularly public facilities and buildings, hospitals, public transportation facilities, restaurants, entertainment facility, rest stops, or any other enclosed space where the public may gather. Relevant surfaces may include floors and wall and other surfaces in a room.

A building may be any building accessible to or used by the public. Relevant surfaces in a building may include tables, counters, doors and doorknobs, elevator buttons, railings, handles, and the like. A building may be a healthcare facility.

A stabilizer may be a chemical that is used to prevent separation or degradation. Stabilizers can include emulsifiers and surfactants, for example, for stabilization of emulsions.

Treat" or other forms of the word, such as "treating," "treatment" or treated," is used here to mean to administer a composition or to perform a method in order to induce, reduce, eliminate, and prevent a characteristic (e.g., inflammation, growth, or viability of viruses). It is generally understood that treating involves providing an effective amount of the composition to the mammal or surface for treatment.

The term "vehicle" or "vehicle carrier" as used herein refers to the manner in which the reagents or compositions may be delivered, including as a liquid, salve, soap, foam, cream, solution, gel, spray, powder, wipes, antiviral treatments, wipes, and the like.

EXAMPLES

Based upon the following in vitro test results, the ethyl ester of protocatechuic acid is an excellent agent for topical disinfection for *Candida auris*, which is otherwise very resistant to known chemicals, including protocatechuic acid. Ethyl ester of protocatechuic acid is known to be safe in low concentrations of 1 to 20 mM on skin. High concentrations are generally to be avoided.

TABLE 1

Protocatechuic acid.

| ORGANISM | RESULTS (mm) Plate 1 | RESULTS (mm) Plate 2 | Average (mm) | Inhibition Type A. |
|---|---|---|---|---|
| *Salmonella enterica* ATCC 14028 | 15 | 13 | 14 | CZ |
| *Clostridium difficile* ATCC 9689 | TBD | TBD | TBD | TBD |
| *Propionibacterium acnes* ATCC 6919 | 23 | 19 | 21 | CZ |
| *Clostridium perfrinqens* ATCC 13124 | 54 | 50 | 52 | CZ |
| *Lactobacillus casei* ATCC 393 | 18 | 24 | 21 | CZ |
| *Candida albicans* ATCC 10231 | 21 | 15 | 18 | CZ |
| *Escherichia coli* ATCC 8739 | 14 | 14 | 14 | CZ |
| *Escerichia coli* ATCC 43895 | 14 | 12 | 13 | CZ |
| *Staphylococcus aureus* ATCC 6538 | 18 | 18 | 18 | CZ |
| Methicillin Resistant *Staphylococcus aureus* ATCC 33591 | 21 | 21 | 21 | CZ |
| *Streptococcus mutans* ATCC 25175 | TBD | TBD | TBD | TBD |
| *Streptococcus ovoqenes* ATCC 19615 | TBD | TBD | TBD | TBD |
| *Staphyloccus epidermidis* ATCC 12228 | 26 | 28 | 27 | CZ |
| *Pseudomonas aeruqinosa* ATCC 9-27 | 13 | 13 | 13 | CZ |
| *Klebsiella pneumoniae* ATCC 4352 | 16 | 13 | 14.5 | CZ |
| MRSE ATCC 51625 | 15 | 20 | 18 | CZ |
| *Apergillus versicolor* ATCC 11730 | TBD | TBD | TBD | TBD |
| *Candida auris* CDC B11903 | NZ | NZ | NZ | NZ |
| *Escherichia coli* 0157:H7 | 17 | 14 | 15.5 | CZ |
| *Listeria monocytogenes* ATCC 13932 | TBD | TBD | TBD | TBD |

NI—No inhibition;
NZ - No zone of Inhibition around the sample;
CZ - Clear zone of inhibition around sample in mm.

TABLE 2

Ethyl ester of protocatechuic acid.

| ORGANISM | RESULTS (mm) Plate I | RESULTS (mm) Plate 2 | Average (mm) | Inhibition Type A. |
|---|---|---|---|---|
| *Salmonella enterica* ATCC 14028 | 28 | 28 | 28 | CZ |
| *Clostridium difficile* ATCC 9689 | TBD | TBD | TBD | TBD |
| *Propionibacterium acnes* ATCC 6919 | 22 | 18 | 20 | CZ |
| *Clostridium perfrinqens* ATCC 13124 | 50 | 54 | 52 | CZ |
| *Lactobacillus casei* ATCC 393 | 24 | 22 | 23 | CZ |
| *Candida albicans* ATCC 10231 | 31 | 28 | 29.5 | CZ |
| *Escherichia coli* ATCC 8739 | 22 | 24 | 23 | CZ |
| *Escerichia coli* ATCC 43895 | 25 | 28 | 27 | CZ |
| *Staphylococcus aureus* ATCC 6538 | 26 | 28 | 27 | CZ |
| Methicillin Resistant *Staphylococcus aureus* ATCC 33591 | 28 | 25 | 26.5 | CZ |
| *Streptococcus mutans* ATCC 25175 | TBD | TBD | TBD | TBD |
| *Streptococcus pyogenes* ATCC 19615 | TBD | TBD | TBD | TBD |
| *Staphyloccus epidermidis* ATCC 12228 | 35 | 35 | 35 | CZ |
| *Pseudomonas aeruqinosa* ATCC 9-27 | 11 | 11 | 11 | CZ |
| *Klebsiella pneumoniae* ATCC 4352 | 28 | 26 | 27 | CZ |
| MRSE ATCC 51625 | 23 | 22 | 23 | CZ |
| *Apergillus versicolor* ATCC 11730 | TBD | TBD | TBD | TBD |
| *Candida auris* CDC 811903 | 31 | 28 | 29.5 | CZ |
| *Escherichia coli* 0157:H7 | 26 | 28 | 27 | CZ |
| *Listeria monocytogenes* ATCC 13932 inhibit ion | TBD | TBD | TBD | TBD |

NI—No inhibition;
NZ - No zone of Inhibition around the sample;
CZ - Clear zone of inhibition around sample in mm.

While this disclosure includes specific examples, it will be apparent after an understanding of the disclosure of this application has been attained that various changes in form and details may be made in these examples without departing from the spirit and scope of the claims and their equivalents.

The invention claimed is:

1. A method of disinfecting *Candida auris* comprising:
treating a surface with a solution comprising 3,4-Dihydroxybenzoic acid ethyl ester.

2. The method of claim 1, wherein the solution further comprises protocatechuic acid.

3. The method of claim 1, wherein the solution comprises an alcohol.

4. The method of claim 1, wherein the alcohol comprises ethanol, or isopropyl alcohol.

5. The method of claim 1, wherein the surface comprises a solid surface, a porous or semi-porous surface, or a cloth-like surface.

6. The method of claim 1, wherein the surface comprises a surface on skin, clothes, masks, a medical device, food processing equipment, a hearing aid, ear plugs, or a surgical implant.

7. The method of claim 1, wherein the surface comprises a surface on a wound dressing, bedding, vascular implants, or bandage.

8. The method of claim 1, wherein the surface comprises a surface in a public building including a floor, wall, table, counter, doorknob, and/or elevator button.

9. The method of claim 1, wherein the public building is a healthcare facility.

10. The method of claim 1, wherein the surface comprises a surface in a ventilation filter, air conditioning or heating duct, or air conditioning or heating component.

11. The method of claim 1, wherein the solution comprises 0.1% to 30% Ethyl ester of Protocatechuic acid in 70% isopropyl alcohol or ethanol.

* * * * *